US006166030A

United States Patent
Macdonald et al.

[11] Patent Number: 6,166,030
[45] Date of Patent: Dec. 26, 2000

[54] COMPOUNDS

[75] Inventors: James MacDonald; James Matz, both of Rochester, N.Y.; William Shakespeare, Framingham, Mass.

[73] Assignee: Astra Aktiebolag, Sodertalje, Sweden

[21] Appl. No.: 09/068,944

[22] PCT Filed: May 5, 1997

[86] PCT No.: PCT/SE98/00792

§ 371 Date: May 21, 1998

§ 102(e) Date: May 21, 1998

[87] PCT Pub. No.: WO98/50380

PCT Pub. Date: Nov. 12, 1998

[30] Foreign Application Priority Data

May 5, 1997 [SE] Sweden ................................ 9701682

[51] Int. Cl.[7] ........................ A61K 31/47; C07D 217/26; C07D 217/00
[52] U.S. Cl. ............................................ 514/307; 546/145
[58] Field of Search ............................. 546/145; 514/307

[56] References Cited

FOREIGN PATENT DOCUMENTS

| 95/05363 | 2/1995 | WIPO . |
| 95/09619 | 4/1995 | WIPO . |
| 95/11231 | 4/1995 | WIPO . |
| 96/01817 | 1/1996 | WIPO . |
| 97/06158 | 2/1997 | WIPO . |

OTHER PUBLICATIONS

Chemical Abstracts 124:289248, MacDonald, 1996.
Chemical Abstracts 126:238314, MacDonald, 1997.
CA 126:238314, MacDonald, 1997.
CA 124:289248, MacDonald, 1996.

*Primary Examiner*—D. Margaret Seaman
*Attorney, Agent, or Firm*—Nixon & Vanderhye

[57] ABSTRACT

There are provided novel compounds of formula (I)

wherein $R^1$ represents a 2-thienyl or 3-thienyl ring and $R^2$ represents C 1 to 4 alkyl and optical isomers and racemates thereof and pharmaceutically acceptable salts thereof; together with processes for their preparation, compositions containing them and their use in therapy. The compounds are selective inhibitors of the neuronal isoform of nitric oxide synthase.

23 Claims, No Drawings

COMPOUNDS

This application is a 371 of PCT/SE98/00792 filed May 5, 1997.

FIELD OF THE INVENTION

This invention relates to new amidine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been implicated in the pathogenesis of inflammatory diseases. Specific regulation of these enzymes should therefore offer considerable potential in the treatment of a wide variety of disease states.

Compounds of various structures have been described as inhibitors of NOS and their use in therapy has been claimed. See, for example, WO 95/09619 (The Wellcome Foundation) and WO 95/11231 (G. D. Searle). The applicant has previously disclosed in WO 95/05363 and WO 96/01817 amidine derivatives which are NOS inhibitors which display some selectivity for inhibition of the neuronal enzyme, ncNOS.

We now disclose a group of amidines that are within the generic scope of WO 96/01817, but which are not specifically exemplified in WO 96/01817. These compounds display surprisingly advantageous properties and are the subject of the present application.

DISCLOSURE OF THE INVENTION

According to the invention we provide a compound of formula (I)

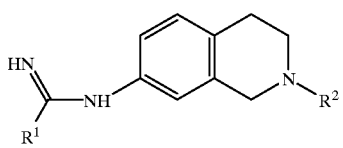

(I)

wherein:
$R^1$ represents a 2-thienyl or 3-thienyl ring;
and R represents C 1 to 4 alkyl;
and optical isomers and racemates thereof and pharmaceutically acceptable salts thereof.
Preferably $R^1$ represents 2-thienyl.
Particularly preferred compounds of the invention include:
N-(2-methyl-1,2,3,4-tetrahydroisoquinolin-7-yl)-2-thiophenecarboximidamide;
N-(2-isopropyl-1,2,3,4-tetrahydroisoquinolin-7-yl)-2-thiophenecarboximidamide;
N-(2-ethyl-1,2,3,4-tetrahydroisoquinolin-7-yl)-2-thiophenecarboximidamide;
N-(2-propyl-1,2,3,4-tetrahydroisoquinolin-7-yl)-2-thiophenecarboximidamide;
N-(2-methyl-1,2,3,4-tetrahydroisoquinolin-7-yl)-3-thiophenecarboximidamide;
and pharmaceutically acceptable salts thereof.

A more especially preferred compound of the invention is:
N-(2-methyl-1,2,3,4-tetrahydroisoquinolin-7-yl)-2-thiophenecarboximidamide;
and pharmaceutically acceptable salts thereof.

Unless otherwise indicated, the term "C 1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

According to the invention, we further provide a process for the preparation of compounds of formula (I), and optical isomers and racemates thereof and pharmaceutically acceptable salts thereof, which comprises:
(a) preparing a compound of formula (I) by reacting a corresponding compound of formula (II)

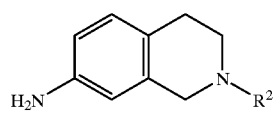

(II)

wherein $R^2$ is as defined above,
with a compound of formula (III) or an acid addition salt thereof

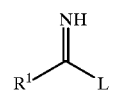

(III)

wherein $R^1$ is as defined above and L is a leaving group;
(b) preparing a compound of formula (I) by reacting a corresponding compound of formula (IV)

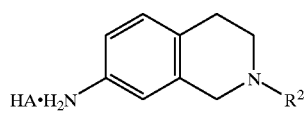

(IV)

wherein $R^2$ is as defined above and HA is an acid,
with a compound of formula (V)

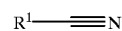

(V)

wherein $R^1$ is as defined above;

(c) preparing a compound of formula (I) by reacting a compound of formula (VI)

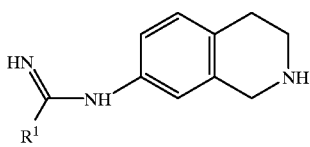

(VI)

wherein $R^1$ is as defined above,
with a compound of formula (VII)

$$R^2—L \quad (VII)$$

wherein $R^2$ represents C 1 to 4 alkyl and L is a leaving group; or
(d) preparing a compound of formula (I) in which $R^2$ represents methyl by reacting a compound of formula (VI) with formaldehyde and formic acid;
and where desired or necessary converting the resultant compound of formula (I), or another salt thereof, into a pharmaceutically acceptable salt thereof, or vice versa, and where desired converting the resultant compound of formula (I) into an optical isomer thereof.

In process (a), the reaction will take place on stirring a mixture of the reactants in a suitable solvent, for example, N-methyl-2-pyrrolidinone or a lower alkanol such as ethanol, isopropanol or tertiary butanol, at a temperature between room temperature and the reflux temperature of the solvent. The reaction time will depend inter alia on the solvent and the nature of the leaving group, and may be up to 48 hours; however it will typically be from 1 to 24 hours. Suitable leaving groups that L may represent include thioalkyl, sulphonyl, trifluoromethyl sulphonyl, halide, alkyl alcohols, aryl alcohols and tosyl groups; others are recited in 'Advanced Organic Chemistry', J. March (1985) 3rd Edition, on page 315 and are well known in the art.

In process (b), the reaction is preferably performed by refluxing a mixture of the two compounds for several hours in the presence of a suitable solvent whereby the reaction temperature is high enough so that condensation takes place readily, but not sufficiently high to decompose the amidine formed. The reaction temperature can vary from room temperature to about 250° C., although it is preferable to perform the reaction at temperatures from about 100° C. to 200° C. We find that o-dichlorobenzene is a particularly suitable solvent. We also find that it is often useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid. We prefer that HA is a hydrohalic acid.

In process (c) the reaction will take place under standard conditions, for example by reacting the two compounds in an inert solvent such as DMF under basic conditions at a suitable temperature, typically room temperature, for a period of up to 72 hours or until the reaction is complete. We have frequently found it desirable to treat the amine with NaH before reacting with the compound of formula (VII). Suitable leaving groups L are mentioned above. We prefer that L represents halide, particularly bromide.

In process (d), the reaction will typically take place on refluxing the reaction mixture for up to 4 hours or until reaction is complete.

Salts of compounds of formula (I) may be formed by reacting the free base or a salt, enantiomer, tautomer or protected derivative thereof, with one or more equivalents of the appropriate acid. The reaction may be carried out in a solvent or medium in which the salt is insoluble, or in a solvent in which the salt is soluble followed by subsequent removal of the solvent in vacuo or by freeze drying. Suitable solvents include, for example, water, dioxan, ethanol, isopropanol, tetrahydrofuran or diethyl ether, or mixtures thereof. The reaction may be a metathetical process or it may be carried out on an ion exchange resin.

The compounds of formula (II) may be prepared by reduction of a corresponding compound of formula (VIII)

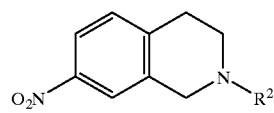

(VIII)

wherein $R^2$ is as defined above.

The reduction reaction may be performed under a number of conditions, for example those described in J. March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure in the presence of a palladium and carbon catalyst until the reaction is complete, typically 3 to 6 hours, or by reduction using zinc metal in acetic acid and methanol.

Compounds of formula (VIII) may be prepared by nitration of a compound of formula (IX)

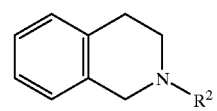

(IX)

wherein $R^2$ is as defined above.

The nitration reaction will take place under conditions well known to a person skilled in the art, for example, on treatment with nitric acid and sulphuric acid or potassium nitrate and sulphuric acid, optionally in an inert organic solvent.

It may also be convenient to prepare compounds of formula (VIII) by nitration of a carbonyl or dicarbonyl derivative of a compound of formula (IX); which nitrated carbonyl or dicarbonyl derivative may be reduced to the desired compound of formula (VIII) using, for example, diborane.

Compounds of formula (VIII) and (IX), as well as certain carbonyl and dicarbonyl derivatives of compounds of formula (IX) just mentioned may also be prepared by one of the numerous methods for preparation of bicyclic heterocyclic compounds.

Thus a compound of formula (X)

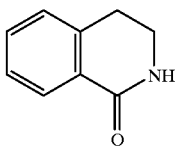

(X)

may be prepared by ring expansion of a cyclic ketone (XI)

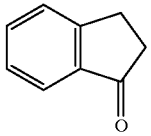

(XI)

by treatment with sodium azide in acid (Grunewald and Dahanukar, *J. Heterocyclic Chem.*, 1994,31, 1609–1617).

It will be apparent to a person skilled in the art that the compounds of formula (X) may also desirably be prepared in nitrated form. Nitration may be achieved by treatment of the non-nitrated analogue with nitric acid and sulphuric acid or potassium nitrate and sulphuric acid under standard conditions.

Intermediate compounds may be prepared as such or in protected form. In particular amine groups may be protected. Suitable protecting groups are described in the standard text "Protective Groups in Organic Synthesis", 2nd Edition (1991) by Greene and Wuts. Amine-protecting groups which may be mentioned include alkyloxycarbonyl such as t-butyloxycarbonyl, phenylalkyloxycarbonyl such as benzyloxycarbonyl, or trifluoroacetate. Deprotection will normally take place on treatment with aqueous base or aqueous acid.

Compounds of formula (VIII) and (IX) in which $R^2$ represents C 1 to 4 alkyl may also be prepared by alkylation of the corresponding N—H compound following process (c) above.

Compounds of formula (IV) may be prepared by analogous processes to those described for the preparation of compounds of formula (II). Compounds of formula (IV) may be converted into corresponding compounds of formula (II) by treatment with a base. Compounds of formula (II) may be converted into corresponding compounds of formula (IV) by treatment with a protic acid HA, for example, one of those listed above.

Compounds of formula (III) are either known or may be prepared by known methods. For example, compounds of formula (III) in which L represents thioalkyl may be prepared by treatment of the corresponding thioamide of formula (XII)

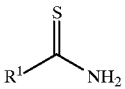

(XII)

wherein $R^1$ is as defined above,
with an alkylhalide under conditions well known to a person skilled in the art.

Alternatively, the acid addition salts of compounds of formula (III) wherein L is thioalkyl may be prepared by reaction of a nitrile of formula (V) with an alkyl thiol and acid, for example hydrochloric acid, in a solvent such as dichloromethane or diethyl ether.

Compounds of formula (V), (VII), (X), (XI) and (XII) are either known or may be prepared by conventional methods known per se.

It will be apparent to a person skilled in the art that it may be desirable to protect an amine or other reactive group in an intermediate compound using a protecting group as described in the standard text "Protective Groups in Organic Synthesis", 2nd Edition (1991) by Greene and Wuts. Suitable amine-protecting groups are mentioned above.

The compounds of the invention and intermediates may be isolated from their reaction mixtures, and if necessary further purified, by using standard techniques.

The compounds of formula (I) may exist in tautomeric, enantiomeric or diastereoisomeric forms, all of which are included within the scope of the invention. The various optical isomers may be isolated by separation of a racemic mixture of the compounds using conventional techniques, for example, fractional crystallisation or HPLC. Alternatively, the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula (I) possess useful nitric oxide synthase inhibiting activity, and in particular, they exhibit good selectivity for inhibition of the neuronal isoform of nitric oxide synthase. They are thus useful in the treatment or prophylaxis of human diseases or conditions in which the synthesis or oversynthesis of nitric oxide by nitric oxide synthase forms a contributory part. Examples of such diseases or conditions include hypoxia, such as in cases of cardiac arrest, stroke and neonatal hypoxia, neurodegenerative conditions including nerve degeneration and/or nerve necrosis in disorders such as ischaemia, hypoxia, hypoglycemia, epilepsy, and in external wounds (such as spinal cord and head injury), hyperbaric oxygen convulsions and toxicity, dementia, for example, pre-senile dementia, Alzheimer's disease and AIDS-related dementia. Sydenham's chorea, Parkinson's disease, Huntington's disease, Amyotrophic Lateral Sclerosis, Korsakoff's disease, imbecility relating to a cerebral vessel disorder, sleeping disorders, schizophrenia, anxiety, depression, seasonal affective disorder, jet-lag, depression or other symptoms associated with Premenstrual Syndrome (PMS), anxiety and septic shock. The compounds of formula (I) are also useful in the treatment and alleviation of acute or persistent inflammatory or neuropathic pain, or pain of central origin, and in the treatment or prophylaxis of inflammation. Compounds of formula (I) are also predicted to show activity in the prevention and reversal of tolerance to opiates and diazepines, treatment of drug addiction and treatment of migraine and other vascular headaches. The compounds of the present invention may also show useful immunosuppressive activity, and be useful in the treatment of gastrointestinal motility disorders, and in the induction of labour. The compounds may also be useful in the treatment of cancers that express nitric oxide synthase.

Compounds of formula (I) are predicted to be particularly useful in the treatment or prophylaxis of hypoxia or stroke or ischaemia or neurodegenerative conditions or schizophrenia or of migraine or for the prevention and reversal of tolerance to opiates and diazepines or for the treatment of drug addiction or for the treatment of pain and especially in the treatment or prophylaxis of hypoxia or stroke or ischaemia or neurodegenerative disorders or schizophrenia or pain. We are particularly interested in conditions selected from the group consisting of hypoxia, ischaemia, stroke, pain, schizophrenia, Parkinson's disease, Huntington's disease and Amyotrophic Lateral Sclerosis.

For the treatment of Parkinson's disease, the compounds of formula (I) are expected to be particularly useful either alone, or in combination with other agents such as L-Dopa.

For the treatment of pain, the compounds of formula (I) are expected to be particularly useful either alone, or in combination with other agents such as opiates, particularly morphine.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

Thus according to a further aspect of the invention we provide a compound of formula (I), or an optical isomer or racemate thereof or a pharmaceutically acceptable salt thereof, for use as a medicament.

According to another feature of the invention we provide the use of a compound of formula (I) or an optical isomer or racemate thereof or a pharmaceutically acceptable salt thereof, in the manufacture of a medicament for the treatment or prophylaxis of the aforementioned diseases or conditions; and a method of treatment or prophylaxis of one of the aforementioned diseases or conditions which comprises administering a therapeutically effective amount of a compound of formula (I), or an optical isomer or racemate thereof or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general, satisfactory results are obtained when the compounds are administered to a human at a daily dosage of between 0.5 mg and 2000 mg (measured as the active ingredient) per day, particularly at a daily dosage of between 2 mg and 500 mg.

The compounds of formula (I), and optical isomers and racemates thereof and pharmaceutically acceptable salts thereof, may be used on their own, or in the form of appropriate medicinal formulations. Administration may be by, but is not limited to, enteral (including oral, sublingual or rectal), intranasal, or topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988.

According to the invention, there is provided a pharmaceutical formulation comprising preferably less than 95% by weight and more preferably less than 50% by weight of a compound of formula (I), or an optical isomer or racemate thereof or a pharmaceutically acceptable salt thereof, in admixture with a pharmaceutically acceptable diluent or carrier. The formulation may optionally also contain a second pharmacologically active ingredient such as L-Dopa, or an opiate analgesic such as morphine.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, that is oesophageal, administration include: tablets, capsules and dragees; sustained release compositions include those in which the active ingredient is bound to an ion exchange resin which is optionally coated with a diffusion barrier to modify the release properties of the resin.

The enzyme nitric oxide synthase has a number of isoforms and compounds of formula (I), and optical isomers and racemates thereof and pharmaceutically acceptable salts thereof, may be screened for nitric oxide synthase inhibiting activity by following procedures based on those of Bredt and Snyder in *Proc. Natl. Acad. Sci.,* 1990, 87, 682–685. Nitric oxide synthase converts $^3$H-L-arginine into $^3$H-L-citrulline which can be separated by cation exchange chromatography and quantified by scintillation counting.

Screen for neuronal nitric oxide synthase inhibiting activity

The enzyme is isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 $\mu$l of the final supernatant is added to each of 96 wells (of a 96 well filter plate) containing either 25 $\mu$l of an assay buffer (50 mM HEPES, 1 mM EDTA, 1.5 mM $CaCl_2$, pH 7.4) or 25 $\mu$l of test compound in the buffer at 22° C. and 25 $\mu$l of complete assay buffer (50 mM HEPES, 1 mM EDTA, 1.5 mM $CaCl_2$, 1 mM DTT, 100 $\mu$M NADPH, 10 $\mu$g/ml calmodulin, pH 7.4). Following a 10 minute equilibration period, 25 $\mu$l of an L-arginine solution (of concentration 18 $\mu$M $^1$H-L-arginine, 96 nM $^3$H-L-arginine) is added to each well to initiate the reaction. The reaction is stopped after 10 minutes by addition of 200 $\mu$l of a slurry of termination buffer (20 mM HEPES, 2 mM EDTA, pH 5.5) and Dowex AG-50W-X8 200-400 mesh.

Labelled L-citrulline is separated from labelled L-arginine by filtering each filter plate and 75 $\mu$l of each terminated reaction is added to 3 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 80% inhibition of nitric oxide synthase at a concentration of 1 $\mu$M, is tested in the assay to verify the procedure.

Screen for endothelial nitric oxide synthase inhibiting activity

The enzyme is isolated from human umbilical vein endothelial cells (HUVECs) by a procedure based on that of Pollock et al in *Proc. Natl. Acad. Sci.,* 1991, 88, 10480–10484. HUVECs were purchased from Clonetics Corp (San Diego, Calif., USA) and cultured to confluency. Cells can be maintained to passage 35–40 without significant loss of yield of nitric oxide synthase. When cells reach confluency, they are resuspended in Dulbecco's phosphate buffered saline, centrifuged at 800 rpm for 10 minutes, and the cell pellet is then homogenised in ice-cold 50 mM Tris-HCl, 1 mM EDTA, 10% glycerol, 1 mM phenylmethylsulphonylfluoride, 2 µM leupeptin at pH 4.2. Following centrifugation at 34,000 rpm for 60 minutes, the pellet is solubilised in the homogenisation buffer which also contains 20 mM CHAPS. After a 30 minute incubation on ice, the suspension is centrifuged at 34,000 rpm for 30 minutes. The resulting supernatant is stored at −80° C. until use.

For the assay, 25 µl of the final supernatant is added to each of 12 test tubes containing 25 µl L-arginine solution (of concentration 12 µM $^1$H-L-arginine, 64 nM $^3$H-L-arginine) and either 25 µl of an assay buffer (50 mM HEPES, 1 mM EDTA, 1.5 mM CaCl$_2$, pH 7.4) or 25 µl of test compound in the buffer at 22° C. To each test tube was added 25 µl of complete assay buffer (50 mM HEPES, 1 mM EDTA, 1.5 mM CaCl$_2$, 1 mM DTT, 100 µM NADPH, 10 µg/ml calmodulin, 12 µM tetrahydrobiopterin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-X8 200-400 mesh column. A 1 ml portion of each terminated reaction mixture is added to an individual 1 ml column and the eluant combined with that from two 1 ml distilled water washes and 16 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthetase at a concentration of 1 µM, is tested in the assay to verify the procedure.

In the screens for nitric oxide synthase inhibition activity, compound activity is expressed as IC$_{50}$ (the concentration of drug substance which gives 50% enzyme inhibition in the assay). IC$_{50}$ values for test compounds were initially estimated from the inhibiting activity of 1, 10 and 100 µM solutions of the compounds. Compounds that inhibited the enzyme by at least 50% at 10 µM were re-tested using more appropriate concentrations so that an IC$_{50}$ could be determined.

When tested in the above screens, the compounds of Examples 1 to 6 below show IC$_{50}$ values for inhibition of neuronal nitric oxide synthase of less than 10 µM and good selectivity for inhibition of the neuronal isoform of the enzyme, indicating that they are predicted to show particularly useful therapeutic activity.

When compared with other compounds, the compounds of formula (I), and optical isomers and racemates thereof and pharmaceutically acceptable salts thereof, have the advantage that they may be less toxic, be more efficacious, be longer acting, have a broader range of activity, be more potent, be more selective for the neuronal isoform of nitric oxide synthase enzyme, produce fewer side effects, be more easily absorbed or have other useful pharmacological properties.

The invention is illustrated by the following examples:

EXAMPLE 1

N-(2-Methyl-1,2,3,4-tetrahydroisoguinolin-7-yl)-2-thiophenecarboximidamide dihydrochloride a) 2-Methyl-7-nitro-1,2,3,4-tetrahydroisoguinoline hydrochloride 7-Nitro-1,2,3,4-tetrahydroisoquinoline (20 g, 93.2 mmol), formaldehyde (37% solution in water, 50 ml) and formic acid (90 ml) were heated at reflux for 1 h, cooled and poured over ice. The reaction mixture was basified with conc. ammonium hydroxide. The precipitated solid was collected, dissolved in warm ethanol (200 ml), acidified with a mixture of 95% ethanol-conc. HCl and the product was left to crystallize. The title compound was obtained as a white solid (18.71 g, 87.8%), m.p. 256–257° C.

b) 2-Methyl-1,2,3,4-tetrahydroisoguinolin-7-ylamine hydrochloride

2-Methyl-7-nitro-1,2,3,4-tetrahydroisoquinoline hydrochloride was dissolved in methanol and hydrogenated at 50 psi in the presence of a catalytic quantity of 10% Pd-C. After 1 h the mixture was filtered through glass and evaporated to provide 2-methyl-1,2,3,4-tetrahydroisoquinolin-7-ylamine hydrochloride, m.p. 137–138° C.

c) 2-Thiophenecarboximidothioic acid, ethyl ester, hydrochloride

To a stirred solution of ethanethiol (28.4 g, 0.45 mols) in methylene chloride (500 ml) at 10° C. under nitrogen was added 2-thiophenecarbonitrile (50.0 g, 0.45 mols). This solution was treated with a slow stream of HCl gas for 6 h. The reaction mixture was then allowed to warm to room temperature for 18 h. Ether (200 ml) was added and a white solid crystallized. The solid 2-thiophenecarboximidothioic acid, ethyl ester, hydrochloride was collected by filtration and air dried (65.8 g), m.p. 196–197° C.

d) N-(2-Methyl-1,2,3,4-tetrahydroisoguinolin-7-yl)-2-thiophenecarboximidamide dihydrochloride 2-Methyl-1,2,3,4-tetrahydroisoquinolin-7-ylamine hydrochloride (34.66 g) in 95% ethanol (600 ml) was warmed to 65° C. to dissolve most of the solids, and the mixture was then allowed to cool with stirring. The next day, the fine suspension of solids was treated with 2-thiophenecarboximidothioic acid, ethyl ester, hydrochloride (41 g) and stirred at 23° C. All solids had dissolved by 2 h, and by 4 h new solids had precipitated. The mixture was treated with concentrated hydrochloric acid (2 ml). The mixture was cooled to 0° C. and stirred for 30 minutes. The solids were filtered off, washed with ethanol (2×50 ml), and air dried to provide N-(2-methyl-1,2,3,4-tetrahydroisoquinolin-7-yl)-2-thiophenecarboximidamide dihydrochloride, m.p. 142–146° C.; MS $^m$/z 272 [M+H]$^+$.

EXAMPLE 2

N-(2-Isopropyl-1,2,3,4-tetrahydroisoquinolin-7-yl)-2-thiophenecarboximidamide

To a stirred solution of N-(1,2,3,4-tetrahydroisoquinolin-7-yl)-2-thiophenecarboximidamide (7.0 g, 21 mmol) in dimethylformamide (100 ml) was added potassium carbonate (14.6 g, 100 mmol). To this mixture was added 2-bromopropane (5.1 g, 42 mmol), and the mixture was then heated to 40° C. for 72 h. The reaction mixture was poured into water (500 ml) and extracted with ethyl acetate (3×100 ml). The combined ethyl acetate extracts were washed with water (200 ml) and dried over magnesium sulfate. Evaporation of the solvent yielded a crude oil, which was then dissolved in hot cyclohexane (250 ml) and ethyl acetate (10 ml). Upon standing the title compound crystallized out and was collected by filtration (3.2 g), m.p. 110–111° C.

EXAMPLE 3

N-(2-Ethyl-1,2,3,4-tetrahydroisoguinolin-7-yl)-2-thiophenecarboximidamide hydrochloride a) 2-Ethyl-7-nitro-1,2,3,4-tetrahydroisoguinoline hydrochloride To 7-nitro-1,2,3,4-tetrahydroisoquinoline (5 g, 30 mmol) in acetonitrile (100 ml) was added ethyl methanesulfonate (6.38 g, 60 mmol) and potassium carbonate (5 g). The mixture was heated to 40° C. for 18 h. The mixture was filtered and concentrated to an oil. The oil was dissolved in methanol and treated with isopropanol-HCl. The hydrochloride salt was collected by filtration (4.89 g, 67%), m.p. 259–260° C.

b) 2-Ethyl-1,2,3,4-tetrahydroisoguinolin-7-ylamine hydrochloride

2-Ethyl-7-nitro-1,2,3,4-tetrahydroisoquinoline hydrochloride (4.89 g) was dissolved in methanol (250 ml) and hydrogenated at 50 psi in the presence of a catalytic quantity of 5% Pd-C. After 1 h the mixture was filtered through glass and evaporated to an oil which was used immediately in the next step.

c) N-(2-Ethyl-1,2,3,4-tetrahydroisoguinolin-7-yl) 2-thiophenecarboximidamide hydrochloride To 2-ethyl-1,2,3,4-tetrahydroisoquinolin-7-ylamine hydrochloride (2.48 g, 10 mmol) in isopropanol (25 ml) was added 2-thiophenecarboximidothioic acid, methyl ester, hydroiodide (5.68 g, 20 mmol). The mixture was heated to 50° C. for 24 h. The mixture was poured into water (50 ml), then basic water (150 ml). The mixture was extracted with ethyl acetate (3×100 ml). The extracts were washed with water, dried with magnesium sulfate, filtered, and concentrated to an oil which crystallized upon standing. The solids were dissolved in ether and treated with isopropanol-HCl. The solids were collected by filtration (1.41 g, 49%), m.p. 122–126° C.

EXAMPLE 4

N-(2-Propyl-1,2,3,4-tetrahydroisoquinolin-7-yl)-2-thiophenecarboximidamide dihydrochloride a) 7-Nitro-2-propyl-1,2,3,4-tetrahydroisoguinoline hydrochloride The title compound was prepared from 7-nitro-1,2,3,4-tetrahydroisoquinoline (5 g, 30 mmol) and 1-bromopropane (7.36 g, 60 mmol) by a procedure analogous to that of Example 3(a). This yielded the hydrochloride salt (3.29 g, 43%), MS $^m$/z 221 [M+H]$^+$.

b) 2-Propyl-1,2,3,4-tetrahydroisoguinolin-7-ylamine hydrochloride

7-Nitro-2-propyl-1,2,3,4-tetrahydroisoguinoline hydrochloride (Example 4(a), 3.29 g, 13 mmol) was hydrogenated using the process described in Example 3(b). The title compound hydrochloride salt thus obtained (3.07 g, 100%) was used immediately in the next step.

c) N-(2-Propyl-1,2,3,4-tetrahydroisoguinolin-7-yl)-2-thiophenecarboximidamide dihydrochloride 2-Propyl-1,2,3,4-tetrahydroisoquinoline-7-ylamine hydrochloride (3.07 g, 13 mmol) in DMF (30 ml) was treated with 2-thiophenecarboximidothioic acid, methyl ester, hydroiodide (2.84 g, 10 mmol) according to the method of Example 3(c). The solids were recrystallized from ether (1.28 g, 43%), MS $^m$/z 300 [M+H]$^+$. The dihydrochloride salt was made by dissolving these solids in ethanol, treating with ethanol-HCl, and triturating with ethyl acetate (0.86 g, 73%), m.p. 241–243° C.

EXAMPLE 5

N-(2-Methyl-1,2,3,4-tetrahydroisoguinolin-7-yl)-3-thiophenecarboximidamide dihydrochloride a) 3-Thiophenecarboximidothioic acid, methyl ester, hydroiodide The title compound was prepared from 3-thiophenecarbothioamide and methyl iodide by a procedure analogous to that described in Example 1(d) of WO 95/05363.

b) N-(2-Methyl-1,2,3,4-tetrahydroisoguinolin-7-yl)-3-thiophenecarboximidamide dihydrochloride A mixture of 2-methyl-1,2,3,4-tetrahydroisoquinolin-7-ylamine hydrochloride (1.5 g, 7.55 mmol) and 3-thiophenecarboximidothioic acid, methyl ester, hydroiodide (2.69 g, 9.44 mmol) in N-methyl-2-pyrrolidinone (10 ml) was heated at 50° C. for 5 h. The resulting solid mass was treated with isopropanol (50 ml), dissolved in water, basified with conc. ammonium hydroxide and extracted twice with chloroform. The combined extracts were dried over magnesium sulphate, the solvent was evaporated and the residue was treated with ethanol-HCl to give the title compound (1.37 g, 52%), MS $^m$/z 272 [M+H]$^+$.

EXAMPLE 6

N-(2-Butyl-1,2,3,4-tetrahydroisoguinolin-7-yl)-2-thiophenecarboximidamide

N-(1,2,3,4-Tetrahydroisoquinolin-7-yl)-2-thiophenecarboximidamide (3.0 g, 9 mmol) and 1-chlorobutane (1.67 g, 18 mmol) were reacted together according to the method of Example 2 except that 95% ethanol was used as the solvent. The crude oil thus obtained was chromatographed on silica gel eluting with 10% methanol-chloroform to give an oil which was crystallized from hot hexane (1.12 g, 40%), m.p. 95–96° C.

What is claimed is:

1. A compound of formula (I)

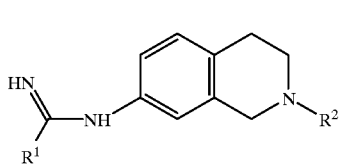

(I)

wherein:

R$^1$ represents a 2-thienyl or 3-thienyl ring; and

R$^2$ represents C$_{1-4}$ alkyl;

or an optical isomer or racemate thereof or a pharmaceutically acceptable salt thereof.

2. A compound of formula (I), according to claim 1, wherein R$^1$ represents 2-thienyl.

3. A compound of formula (I), according to claim 1, wherein R$^2$ represents methyl.

4. A compound of formula (I), according to claim 1, wherein R$^1$ represents 2-thienyl and R$^3$ represents methyl.

5. A compound of formula (I) which is:

N-(2-methyl-1,2,3,4-tetrahydroisoquinolin-7-yl)-2-thiophenecarboximidamide;

N-(2-isopropyl-1,2,3,4-tetrahydroisoquinolin-7-yl)-2-thiophenecarboximidamide;

N-(2-ethyl-1,2,3,4-tetrahydroisoquinolin-7-yl)-2-thiophenecarboximidamide;

N-(2-propyl-1,2,3,4-tetrahydroisoquinolin-7-yl)-2-thiophenecarboximidamide;

N-(2-methyl-1,2,3,4-tetrahydroisoquinolin-7-yl)-3-thiophenecarboximidamide;

N-(2-butyl-1,2,3,4-tetrahydroisoquinolin-7-yl)-2-thiophenecarboximidamide;

or an optical isomer or racemate of any one thereof or a pharmaceutically acceptable salt of any one thereof.

6. A pharmaceutical formulation comprising a compound of formula (I), as defined in claim 1, or an optical isomer or racemate thereof or a pharmaceutically acceptable salt thereof, optionally in admixture with a pharmaceutically acceptable diluent or carrier.

7. A pharmaceutical formulation comprising a compound of formula (I), as defined in claim 1, or an optical isomer or racemate thereof or a pharmaceutically acceptable salt thereof, in combination with L-Dopa, or with an opiate analgesic, optionally in admixture with a pharmaceutically acceptable diluent or carrier.

8. A method of treating, or reducing the risk of, a human disease or condition in which inhibition of nitric oxide synthase activity is beneficial which comprises administering to a person suffering from or susceptible to such a disease or condition, a therapeutically effective amount of a compound of formula (I), as defined in claim 1, or an optical isomer or racemate thereof or a pharmaceutically acceptable salt thereof.

9. A method of treatment according to claim 8 in which it is predominantly the neuronal isoform of nitric oxide synthase that is inhibited.

10. A method of treating, or reducing the risk of, hypoxia or stroke or ischaemia or neurodegenerative conditions or schizophrenia or pain or migraine, or for the prevention and reversal of tolerance to opiates and diazepines, or for the treatment of drug addiction which comprises administering to a person suffering from or susceptible to such a disease or condition a therapeutically effective amount of a compound of formula (I), as defined in claim 1, or an optical isomer or racemate thereof or a pharmaceutically acceptable salt thereof.

11. A method of treatment according to claim 10, wherein the condition to be treated is selected from the group consisting of hypoxia, ischaemia, stroke, Huntington's disease, Parkinson's disease, Amyotrophic Lateral Sclerosis, schizophrenia and pain.

12. A method of treatment according to claim 11, wherein the condition to be treated is stroke.

13. A method of treatment according to claim 11, wherein the condition to be treated is Amyotrophic Lateral Sclerosis.

14. A method of treatment according to claim 11, wherein the condition to be treated is pain.

15. A method of treatment according to claim 11, wherein the condition to be treated is Huntington's disease.

16. A method of treatment according to claim 11, wherein the condition to be treated is Parkinson's disease.

17. A method of treatment according to claim 11, wherein the condition to be treated is schizophrenia.

18. A method of treating, or reducing the risk of suffering from, pain which comprises administering to a person suffering from or at risk of suffering from, pain a therapeutically effective amount of a compound of formula (I), as defined in claim 1, or an optical isomer or racemate thereof or a pharmaceutically acceptable salt thereof, in combination with an opiate analgesic agent.

19. A method of treatment of Parkinson's disease which comprises administering to a person suffering from, or at increased risk of suffering from, Parkinson's disease, a therapeutically effective amount of a compound of formula (I), as defined in claim 1, or an optical isomer or racemate thereof or a pharmaceutically acceptable salt thereof, in combination with L-Dopa.

20. A process for the preparation of a compound of formula (I), as defined in claim 1, and optical isomers and racemates thereof and pharmaceutically acceptable salts thereof, which comprises:

(a) preparing a compound of formula (I) by reacting a corresponding compound of formula (II)

(II)

wherein $R^2$ is as defined in claim 1,
with a compound of formula (III) or an acid addition salt thereof (III)

wherein $R^1$ is as defined in claim 1 and L is a leaving group;

(b) preparing a compound of formula (I) by reacting a corresponding compound of formula (IV)

(IV)

wherein $R^2$ is as defined in claim 1 and HA is an acid, with a compound of formula (V)

(V)

$R^1$—≡N wherein $R^1$ is as defined in claim 1;

(c) preparing a compound of formula (I) by reacting a compound of formula (VI)

(VI)

wherein $R^1$ is as defined in claim 1,
with a compound of formula (VII)

$R^2$—L          (VII)

wherein $R^2$ is as defined in claim 1 and L is a leaving group; or (d) preparing a compound of formula (I) in which $R^2$ represents methyl by reacting a compound of formula (VI) with formaldehyde and formic acid;

and where desired or necessary converting the resultant compound of formula (I), or another salt thereof, into a pharmaceutically acceptable salt thereof, or vice versa, and where desired converting the resultant compound of formula (I) into an optical isomer thereof.

21. A pharmaceutical formulation according to claim 7, wherein said opiate analgesic is morphine.

22. A method of treatment according to claim 18, wherein said opiate analgesic agent is morphine.

23. A method of treatment according to claim 10, wherein the condition to be treated is migraine.

* * * * *